United States Patent [19]

Tokura et al.

[11] Patent Number: 5,011,987
[45] Date of Patent: Apr. 30, 1991

[54] PROCESS FOR MANUFACTURING HIGH-PURITY O-TOLUIC ACID

[75] Inventors: Nobuyuki Tokura; Tadayoshi Takefumi; Shunichi Matsumoto; Yoshihiro Shiokawa, all of Kurashiki, Japan

[73] Assignee: Mitsubishi Gas Chemical Company, Tokyo, Japan

[21] Appl. No.: 523,868

[22] Filed: May 15, 1990

[30] Foreign Application Priority Data

May 17, 1989 [JP] Japan .................. 64-121590

[51] Int. Cl.$^5$ ............................................. C07C 51/42
[52] U.S. Cl. ............................................ 562/494
[58] Field of Search .................... 562/494; 560/209

[56] References Cited

U.S. PATENT DOCUMENTS

| | | | |
|---|---|---|---|
| 2,653,165 | 9/1953 | Levine | 260/475 |
| 2,712,549 | 7/1955 | Cheney | 260/524 |
| 2,712,551 | 7/1955 | Himel | 260/524 |
| 2,723,995 | 11/1955 | Rutherford | 260/524 |
| 2,785,199 | 3/1957 | Himel | 562/494 |
| 2,906,775 | 9/1959 | Taplin et al. | 260/524 |
| 3,235,588 | 2/1966 | Weaver | 562/494 |
| 3,607,920 | 9/1971 | Clark | 260/524 |
| 4,092,353 | 5/1978 | Wolf | 562/494 |

FOREIGN PATENT DOCUMENTS

| | | |
|---|---|---|
| 547010 | 10/1957 | Canada . |
| 553081 | 2/1958 | Canada . |
| 52-46217 | 11/1977 | Japan . |
| 53-112831 | 10/1978 | Japan . |
| 56-55341 | 5/1981 | Japan . |
| 63-141945 | 6/1988 | Japan . |

OTHER PUBLICATIONS

Patent Abstracts of Japan, unexamined applications, C Section vol. 12, No. 398 Oct. 21, 1988, The Patent Office Japanese Government, p. 115 C 538 Kokai-No. 63-141 945 (Mitsubishi Gas Chem).

*Primary Examiner*—Paul J. Killos
*Attorney, Agent, or Firm*—Melvin I. Stoltz

[57] ABSTRACT

A process for manufacturing high-purity o-toluic acid from a partial oxidation product of o-xylene is disclosed. o-Toluic acid is widely used as a raw material for agricultural chemicals, medicines, polymerization initiators, and the like. Depending on its use, 99% by weight or more purity is demanded for o-toluic acid. Hitherto, o-toluic acid having purity of higher than 99% by weight could not be obtained by fractionation, and purification by fractional crystallization was used. Fractional crystallization is, however, and expensive operation and not only gives a low yield of product but also results a large amount of waste water. The process disclosed herein gives an economical, commercial way to obtain high purity o-toluic acid. In summary, a process for the manufacture of high purity o-toluic acid which comprises: subjecting an oxidation product of o-xylene to distillation to remove therefrom low boiling point components such as unreacted o-xylene and benzoic acid, and high boiling point components, of which the major component is o-methylbenzyl o-toluate, thus obtaining crude o-toluic acid, treating said crude o-toluic acid with ammonia of an amount 1 to 1.2 mol equivalent of o-phthalic acid contained in said crude o-toluic acid, and subjecting the product thus treated to distillation is disclosed.

15 Claims, 1 Drawing Sheet

PROCESS FOR MANUFACTURING HIGH-PURITY O-TOLUIC ACID

BACKGROUND OF THE INVENTION

1. Field of the Invention

This invention relates to a process for manufacturing high-purity o-toluic acid from o-xylene. o-Toluic acid is widely used as a raw material for agricultural chemicals, medicines, polymerization initiators, and the like. Depending on its use, 99% by weight or more purity is demanded for o-toluic acid.

2. Description of the Prior Art o-Toluic acid is produced by oxidizing o-xylene. Normally, a liquid oxidation process (hereinafter referred to from time to time as "liquid-phase air oxidation process") in which o-xylene is oxidized by a molecular oxygen-containing gas using a heavy metal salt of an organic acid such as cobalt naphthenate, cobalt toluate, manganese toluate, or the like as a catalyst. These processes are wholly described in U.S. Pat. No. 2,653,165, U.S. Pat. No. 2,712,549, U.S. Pat. No. 2,712,551, etc.

Japanese Patent Publication No. Sho 52 (1977)-46217 and Japanese Patent Application Laid-open No. Sho 53 (1978)-112831 disclose processes for suppressing side reactions in the above liquid oxidation process. Japanese Patent Application Laid-open No. Sho 56 (1981)-55341 describes a process for the purification of the oxidation product by recrystallization.

The reaction product obtained by the oxidation of o-xylene contains, besides o-toluic acid and water, benzoic acid, phthalide, o-phthalic acid, o-tolualdehyde, o-methylbenzyl alcohol and its ester, and the like as by-products. Thus, the product must be purified by means of solvent extraction, crystallization, distillation, or the like.

Among these processes, distillation is the simplest and easiest process from the aspect of the industrial scale operation. However, separation of o-phthalic acid and phthalide from o-toluic acid by distillation is difficult, because of proximity of their boiling points and formation of azeotropic mixtures. Producing o-toluic acid having a purity of 99% by weight or more in an industrial scale by distillation is unfeasible.

Because of this, in a conventional process of producing high-purity o-toluic acid, the oxidation reaction product of o-xylene is usually, after recovery of unreacted o-xylene therefrom, subjected to a crystallization process for purification, in which crude o-toluic acid is dissolved in a large amount of hot water, followed by cooling to crystallize high-purity o-toluic acid. This purification, however, achieves only a low yield, since a portion of o-toluic acid is dissolved and remained in waste water together with by-products. The o-toluic acid dissolved in the waste water is unrecovered and discharged. Thus, a large amount of waste water which requires activated sludge treatment is formed, and increases the production cost and labor.

SUMMARY OF THE INVENTION

In order to overcome these problems in the production of high purity o-toluic acid from oxidation product of o-xylene, we previously found a process in which oxidation product of o-xylene is treated with ammonia to convert o-phthalic acid to phthalimide and then the oxidation product treated with ammonia is subjected to distillation. We have filed an application for patent based on that invention (Japanese Patent Application Laid-open No. Sho 63 (1988)-141945).

Further investigations on that process using a experimental pilot plant by us have proven that the consumption of ammonia was greater than the theoretical amount, and that the yield and purity of o-toluic acid were still not sufficiently high, although o-phthalic acid was effectively removed by selective, preferential imidation to form o-phthalimide. Furthermore, the investigations revealed a considerable fluctuation and poor reproducibility in the operation results. We discovered that the fluctuation in the ammonia consumption and the yield and purity of o-toluic acid exhibited certain correlations with the content of o-methylbenzyl o-toluate which is an ester contained in the oxidation product of o-xylene.

We have undertaken further studies and found that, according to the reaction shown in the following schemata, (i) o-methylbenzyl o-toluate, which is an ester of o-methylbenzyl alcohol and o-toluic acid and which is a by-product in the liquid phase air oxidation of o-xylene, reacted with ammonia in the above-mentioned treatment to produce o-toluamide and o-methylbenzyl alcohol, thus increasing the amount of ammonia consumed in the reaction, and (ii) o-methylbenzyl alcohol thus produced further reacted with o-toluic acid to produce the ester, resulting in the decrease in the yield of o-toluic acid.

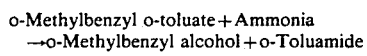
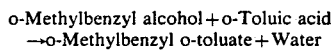

o-Methylbenzyl o-toluate + Ammonia
→o-Methylbenzyl alcohol + o-Toluamide  [I]

o-Methylbenzyl alcohol + o-Toluic acid
→o-Methylbenzyl o-toluate + Water  [II]

We have further found that o-toluamide which is produced in the above reactions was dehydrated in the distillation operation to produce o-tolunitrile.

o-Toluamide (Heating)→ o-Tolunitrile + Water  [III]

Because of its low boiling point, o-tolunitrile goes up along with o-toluic acid in a distillation column for the separation of o-toluic acid and high boiling point components such as o-phthalimide, etc. This results in decrease in the purity and the yield of o-toluic acid.

That is to say, the pilot plant experiments by us revealed the fact that the addition of ammonia of an amount equivalent to o-phthalimide, etc. This results in decrease in the purity and the yield of o-toluic acid.

That is to say, the pilot plant experiments by us revealed the fact that the addition of ammonia of an amount equivalent to o-phthalic acid contained in crude o-toluic acid which was prepared by oxidation of o-xylene could eliminate o-phthalic acid only incompletely in the final o-toluic acid product, so long as such an oxidation product contain o-methylbenzyl o-toluate even if light components such as unreacted o-xylene, benzoic acid, etc. were removed in advance. Use of an excess amount of ammonia for the complete elimination of o-phthalic acid from o-toluic acid product not only results in the decrease in the o-toluic acid yield due to formation of o-tolunitrile, but also produces o-toluic acid product having a lower purity because of contamination of o-tolunitrile in the final o-toluic acid product.

Removal of o-methylbenzyl o-toluate by distillation in advance of ammonia treatment, therefore, raises both the purity and yield of o-toluic acid without the use of an excess amount of ammonia. These findings have led to the completion of the present invention.

Accordingly, an object of this invention is to provide an economical process for the manufacture of high purity o-toluic acid by the liquid phase oxidation of o-xylene with a molecular oxygen-containing gas.

Another object of this invention is to provide a simple, continuous, industrially applicable process for the manufacture of high purity o-toluic acid from crude product obtained by the liquid phase air-oxidation of o-xylene without forming a large amount of waste water which is very troublesome to treat.

Other objects, features and advantages of this invention will hereinafter become more readily apparent from the following description.

That is, the gist of this invention resides in a process for the manufacture of high purity o-toluic acid which comprises:
  subjecting an oxidation product of o-xylene to distillation to remove therefrom low boiling point components such as unreacted o-xylene and benzoic acid, and high boiling point components, of which the major component is o-methylbenzyl o-toluate, thus obtaining crude o-toluic acid,
  treating said crude o-toluic acid with ammonia of an amount 1 to 1.2 mol equivalent of o-phthalic acid contained in said crude o-toluic acid, and
  subjecting the product thus treated to distillation.

DETAILED DESCRIPTION OF THE INVENTION

Figure 1:
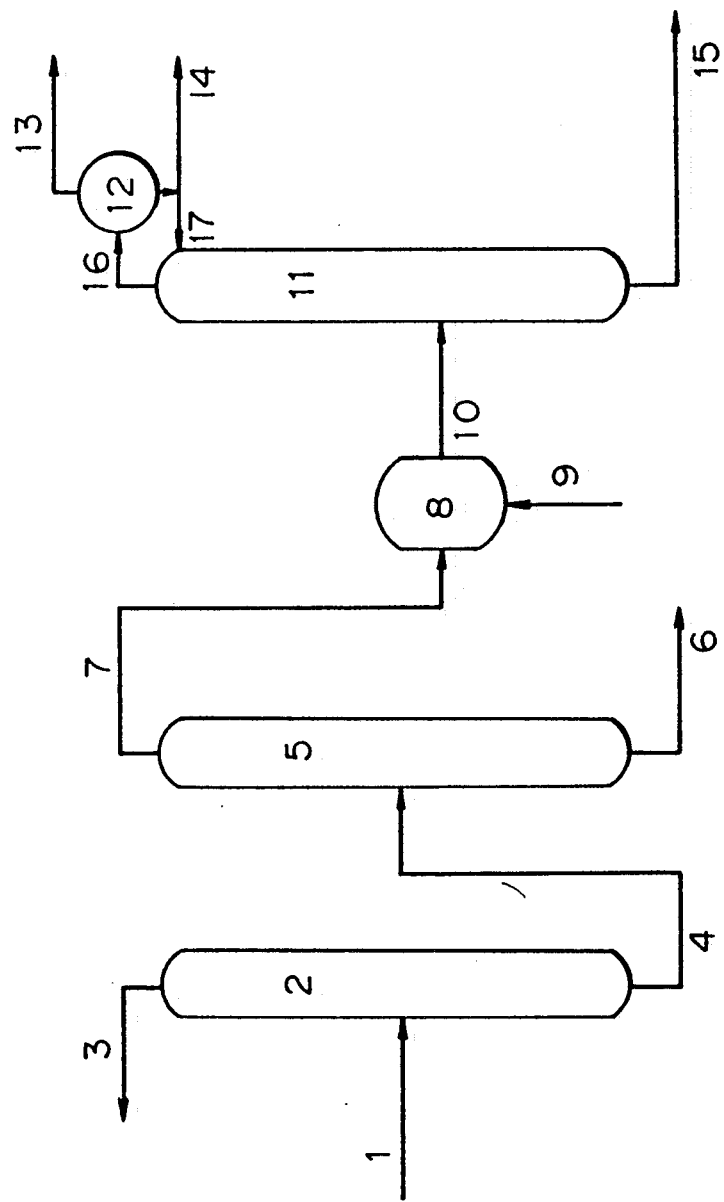
FIG. 1 is a simplified schematic flow diagram of a plant suitable for carrying out the process of this invention, from which any equipment unnecessary for the illustration of this invention such as pumps, heat exchangers, reflux drums, reboilers, and the like are omitted.

Oxidation of o-xylene in this invention is carried out according to a conventional process. Specifically, o-xylene is oxidized in liquid phase in the absence of solvent by a molecular oxygen-containing gas using a heavy metal salt of organic acid such as cobalt naphthenate, cobalt toluate, manganese toluate, or the like as a catalyst. The reaction temperature is normally 100° to 260° C., and preferably 100° to 220° C. Pressure increases as the reaction temperature increases. Usually, pressure in the range of 0 to 30 Kg/cm$^2$G is employed, with the preferable range being 0 to 25 Kg/cm$^2$G. The reaction time is usually between 0.5 to 5 hours, and preferably between 1 to 3 hours.

As can be understood from the above description, this invention has been developed for the purpose of commercial application of the prior invention disclosed in Japanese Patent Application Laid-open No. Sho 63 (1988)-141945 which had been completed by us based on the laboratory experimental results. When crude o-toluic acid to be used in the process of this invention is that prepared by a laboratory scale unit by the liquid-phase air oxidation of o-xylene and contains a smaller amount of impurities, particularly o-methylbenzyl o-toluate, the effect of the invention is not so remarkable. On the other hand, the effect of the process is outstanding when crude o-toluic acid contains a larger amount of o-methylbenzyl o-toluate, as is frequently encountered in o-toluic acid produced in commercial o-xylene oxidation units. Crude o-toluic acid obtained from commercial o-xylene oxidation units very frequently contains 8% by weight or more of o-methylbenzyl o-toluate, and the process of this invention can be effectively applied to crude o-toluic acid which contains 3% by weight or more of o-methylbenzyl o-toluate.

In the present invention, an oxidation reaction product of o-xylene is firstly subjected to distillation or distillations to recover unreacted o-xylene and to eliminate low boiling point components such as benzoic acid, etc., and further to remove higher boiling point components, of which the major component is o-methylbenzyl o-toluate, and then the crude o-toluic acid thus obtained is treated with ammonia following which or concurrent with the ammonia treatment the crude o-toluic acid is again submitted to distillation.

A plate column or a packed column having 3 or more theoretical plates is used for the recovery of unreacted o-xylene (such a column is hereinafter referred to as the first distillation column). A column having 3 to 5 theoretical plates is preferable. Distillation is carried out at 30 to 60 Torr. and 150° to 200° C. The raw material is fed to the column at a point of approximately middle portion or somewhat lower part thereof and at a point which allocates at least one theoretical plate for the stripping section. A preferable reflux ratio is between 0.1 and 1.

A second distillation column having 5 or more theoretical plates is provided to remove higher boiling point components, of which the major component is o-methylbenzyl o-toluate (hereinafter referred to simply as "ester"). Preferably, a plate column or a packed column having 5 to 10 theoretical plates is used. The column is operated at 10 to 40 Torr. and 150° to 230° C. It is desirable that the feed from the bottom of the first distillation column be fed into the second distillation column at a point lower than the middle portion, the point which allocates at least one theoretical plate for the stripping section. A preferable reflux ratio is between 0.1 and 1.

Besides the system illustrated above, in which removal of low boiling point components and the ester is performed in two distillation columns, a system using a single distillation column can be used. In this case, the low boiling point components containing unreacted o-xylene, etc. are recovered from the top, crude o-toluic acid is recovered in a liquid state as the side-cut stream, and a high boiling point component containing the ester is removed from the bottom of the column. For the single column for this purpose, a plate column or a packed column having 7 or more theoretical plates is used. A column having 7 to 15 theoretical plates is preferable. The column is operated at 30 to 40 Torr. and 150° to 230° C. It is desirable that the feed be charged at a lower part of the column to allocate at least one theoretical plate for the stripping section and that crude o-toluic acid be drawn at an upper point higher than the middle portion and lower than 1/5 of the column length from the top of the column. In the operation using only one distillation column, in usual cases, a sufficient reflux ratio may be obtained automatically. A preferable amount of reflux is between 0.1 and 1 times based on the total amount of the light component recovered at the top and the crude o-toluic acid withdrawn as the side-cut stream. Crude o-toluic acid which is drawn from the column as the side-cut stream may be subjected to a stripping operation. The difference in boiling points of the ester and o-toluic acid is great enough to separate the two compounds almost completely. Recovery of o-toluic acid in this operation is about 99.8%.

For the treatment with ammonia, any kinds of ammonia-containing gas such as gaseous ammonia or liquefied ammonia and ammonia-containing solution such as aqueous ammonia or aqueous solution of ammonium carbonate can be employed. The treatment is carried out at a temperature of 95° to 240° C., preferably 110° to 240° C., and most preferably 180° to 220° C., under either a reduced or normal pressure.

The crude o-toluic acid obtained by liquid-phase air oxidation of o-xylene usually keeps a liquid state even at 95° C. since it contains a considerable amount of impurities. Sometimes, however, it solidifies around 100° C. and is so viscous that mixing the ammonia is difficult at this temperature. A preferable temperature of the ammonia treatment is therefore 110° C. or higher. At a temperature higher than 240° C., however, the problems such as decomposition or polymerization of o-toluic acid, or excessive reactions of o-toluic acid with ammonia may occur. An amount of ammonia of 1.0 to 1.2 mole equivalent to o-phthalic acid contained in crude o-toluic acid is used for the treatment. With an amount of ammonia smaller than this range, some amount of o-phthalic acid may remain in o-toluic acid after the treatment. If the amount exceeds this range, o-tolunitrile may be contained in the o-toluic acid product, and also decreases the yield of the product.

When aqueous ammonia or an aqueous solution of ammonium carbonate, which has a considerably low reactivity, is used as an ammonia source, the amount used for the treatment must be adjusted taking the reactivity of ammonia in these sources into account. In general, only as much as 50% ammonia contained in aqueous ammonia or an aqueous solution of ammonium carbonate is involved in the reaction.

As a means for the ammonia treatment, either a method of adding ammonia gas or ammonia solution to the o-toluic acid to be fed to a fractionator (a third distillation column) and agitating the mixture, a method of mixing the feed to the fractionator with ammonia using a line mixer, a method of injecting ammonia at the bottom of the fractionator, or the like can be used.

Next, the ammonia-treated crude o-toluic acid is subjected to fractionation so as to separate pure o-toluic acid from high boiling point components such as o-phthalimide, phthalide, etc. As to the fractionator, a packed column or a plate column having 10 ore more theoretical plates can be used. Preferably, a plate column or a packed column having 10 to 30 theoretical plates is used as the fractionator and operated at 100 to 300 Torr., preferably 150 to 250 Torr., and a reflux ratio of about 3 to 20. If the pressure is smaller than 100 Torr., an azeotrope of o-toluic acid and phthalide is produced, thus impairing the purity of o-toluic acid. A higher pressure elevates the bottom temperature of the fractionator, in which case o-toluic acid tends to decompose or polymerize. The fractionator should, therefore, be operated at the bottom temperature of lower than 250° C. Crude o-toluic acid treated with ammonia is fed to the fractionator at a point below the middle of the column and where at least two, preferably three, theoretical plates are allocated for the stripping section. For example, when a distillation column with 30 theoretical plates is used, it is preferable to allocate 3 to 7 theoretical plates in the stripping section.

The invention will hereafter be described with reference to FIG. 1, which shows a typical schematic flow of the process for manufacturing high purity o-toluic acid according to the present invention. The reaction product of liquid phase oxidation of o-xylene is fed to the first distillation column 2 iva line 1. A substantial portion of unreacted o-xylene, intermediate products, benzoic acid, and the like is discharged via line 3 for the recovery. A liquid containing o-toluic acid is sent to the second distillation column 5 via line 4, where it is distilled to obtain crude o-toluic acid from the top via line 7, while removing high boiling components containing the ester from the bottom via line 6. Crude o-toluic acid from the top of the second distillation column is sent, after cooled and condensed, to an ammonia mixer 8 via line 7, where it is mixed with ammonia which is fed to the mixer 8 via line 9. The mixture is sent to the third distillation column (a fractionator) 11 via line 10, where the vapor obtained from the top via line 16 is partially condensed in the partial condenser 12. Low boiling point components not condensed in the condenser 12, such as benzoic acid, is removed via line 13. A portion of the condensed liquid is recovered via line 14 as purified o-toluic acid, with the remaining portion being recycled to the top of the third distillation column 11 via line 17 as the reflux. Phthalimide, phthalide, and the like are separated from the bottom of the third distillation column 11 via line 15.

Unlike the crystallization method, by the process of the present invention, high purity o-toluic acid can easily be manufactured with a very small amount of loss. Since the by-products can be obtained at a high concentration, they can easily be treated for disposal by burning, etc., without the need for the activated sludge treatment.

Moreover, since the process of the present invention can be continuously conducted by distillation operations without complicated procedure, it can contribute labor saving and greatly reduce the cost for o-toluic acid purification.

DESCRIPTION OF PREFERRED EMBODIMENTS

In the followings, the present invention will be materially described by way of Examples. Of course, these Examples are given for illustration purpose only and the present invention will not be limited thereto.

EXAMPLE 1

An o-xylene oxidation product manufactured under a pressure of 5 Kg/cm$^2$G and at a temperature of 160° C. by using cobalt naphthenate as a catalyst was purified by the process shown in FIG. 1. A packed column packed with 1 inch pall rings to give 4 theoretical plates was used as the first distillation column. The raw materials was fed at the position to allocate 3 theoretical plates in the enriching section and 1 theoretical late in the striping section. The distillation column was operated at the column top pressure of 50 Torr., column top temperature of 120° C., bottom temperature of 180° C. and a reflux ratio of 0.3, thus removing the most portion of the unreacted o-xylene, intermediate products, and benzoic acid. A packed column packed with 1 inch pall rings to give 8 theoretical plates was used as the second distillation column. The bottom stream of the first distillation column was fed to the second distillation column at the point to allocate 6 theoretical plates in the enriching section and 2 plates in the gripping section. The distillation column was operated at column top pressure of 20 Torr., column top temperature of 151° C., bottom temperature of 185° C. and a reflux ratio of 0.5 to remove high boiling point components containing the ester as the major component from the bottom, thereby recovered crude o-toluic acid from the top of the column.

Ammonia gas equimolar to phthalic acid contained in the crude o-toluic acid was added to the crude o-toluic acid obtained in the second distillation column and stirred at 200° C. The mixture was charged to the third distillation column (fractionator) packed with 1 inch pall rings to give 30 theoretical plates at the point to allocate 25 theoretical plates in the enriching section and 5 theoretical plates in the stripping section. The mixture was distilled at the column top pressure of 120 Torr., column top temperature of 189° C., bottom temperature of 240° C. and a reflux ratio of 10 to recover purified o-toluic acid having a purity of 99.7% at a recovery rate of 95%. Incidentally, the "recovery rate" throughout Examples means the percentage of pure o-toluic acid contained in the produced o-toluic acid per pure o-toluic acid contained in the bottom stream of the first distillation column.

EXAMPLE 2

This examples is not within the scope of the present invention and is given for comparative purpose only.

Crude o-toluic acid used in Example 1 was purified in the same manner as in Example 1, except that removal of high boiling point components in the second distillation column was omitted. Purified o-toluic acid having a purity of 99.6% was recovered from the top of the fractionator at a recovery rate of 90%.

EXAMPLE 3

This example is not within the scope of the present invention and is given for comparative purpose only.

Crude o-toluic acid used in Example 1 was purified in the same manner as in Example 2, except that the treatment with ammonia was omitted. Purified o-toluic acid having a purity of 97.5% was recovered from the top of the fractionator at a recovery rate of 91%.

EXAMPLE 4

Instead of the treatment with ammonia gas in Example 1, an aqueous solution of ammonia (concentration: 2%) in an amount of 2.15 equivalent mol of o-phthalic acid contained in the crude o-toluic acid was added and heated with stirring at 100° C. for about 10 minutes. The distillation conditions were the same as in Example 1. Purified o-toluic acid having a purity of 99.6% was recovered from the top of the fractionator at a recovery rate of 94%.

Results of analysis (% by weight) of crude o-toluic acid, the product after ammonia treatment, and purified o-toluic acid are given in Table 1, in which the following abbreviations were used.

OTA: o-toluic acid;
PA: o-phthalic acid;
PL: phthalide;
EST: o-methybenzyl o-toluate;
Others: other components, including benzoic acid, phthalimide, etc.

TABLE 1

|  | OTA | PA | PL | EST | Others |
|---|---|---|---|---|---|
| Example 1 |  |  |  |  |  |
| Crude OTA | 90.11 | 3.34 | 5.03 | 0.02 | 1.50 |
| Product after NH$_3$ treatment | 90.23 | 0.03 | 4.98 | 0.03 | 4.73 |
| Purified OTA | 99.72 | 0.04 | 0.15 | — | 0.09 |
| Example 2 |  |  |  |  |  |
| Crude OTA | 85.67 | 3.27 | 4.50 | 4.26 | 2.30 |
| Product after NH$_3$ treatment | 86.03 | 0.18 | 4.73 | 4.39 | 4.67 |
| Purified OTA | 99.58 | 0.07 | 0.13 | — | 0.22 |
| Example 3 |  |  |  |  |  |
| Crude OTA | 85.67 | 3.27 | 4.50 | 4.26 | 2.30 |
| Purified OTA | 97.50 | 2.11 | 0.23 | — | 0.16 |
| Example 4 |  |  |  |  |  |
| Crude OTA | 90.11 | 3.34 | 5.03 | 0.02 | 1.50 |
| Product after NH$_3$ treatment | 89.97 | 0.15 | 5.21 | 0.04 | 4.63 |
| Purified OTA | 99.61 | 0.06 | 0.18 | — | 0.15 |

Obviously, numerous modifications and variations of the present invention are possible in the light of the above teachings. It is therefore to be understood that within the scope of the appended claims, the invention may be practiced otherwise than as specifically described herein.

What is claimed is:

1. A process for the manufacture of high purity o-toluic acid which comprises:
   subjecting an oxidation product of o-xylene to distillation to remove therefrom low boiling point components such as unreacted o-xylene and benzoic acid, and high boiling point components, of which the major component is o-methybenzyl o-toluate, thus obtaining crude o-toluic acid,
   treating said crude o-toluic acid with ammonia of an amount 1 to 1.2 mole equivalent of o-phthalic acid contained in said crude o-toluic acid, and
   subjecting the product thus treated to distillation.

2. A process according to claim 1, wherein said distillation for removing said low boiling point components such as unreacted o-xylene and benzoic acid and is carried out using a first distillation column having 3 or more theoretical plates.

3. A process according to claim 1, wherein said distillation for removing said low boiling point components such as unreacted o-xylene and benzoic acid is carried out using a first distillation column having 3 to 5 theoretical plates, to which the raw material is fed at a point of approximately middle portion or somewhat lower part thereof and at a point which allocates at least one theoretical plate for the stripping section, under a pressure of 30 to 60 Torr., at a temperature of 150° to 200° C., and at a reflux ratio of 0.1 to 1.

4. A process according to claim 1, wherein said distillation for removing said high boiling point components, of which the major component is o-methylbenzyl o-toluate, is carried out using a second distillation column having 5 or more theoretical plates.

5. A process according to claim 3, wherein said distillation for removing said high boiling point components, of which the major component is o-methylbenzyl o-toluate, is carried out using a second distillation column having 5 to 10 theoretical plates, to which the feed from the bottom of the first distillation column is fed at a point lower than the middle portion, the point which allocates at least one theoretical plate for the stripping section, under a pressure of 10 to 40 Torr., at a temperature of 150 to 230° C., and at a reflux ratio of 0.1 to 1, thus obtaining the crude o-toluic acid from the top of the second distillation column.

6. A process according to claim 1, wherein said distillation for removing said low boiling point components such as unreacted o-xylene and benzoic acid, and said high boiling point components, of which the major component is o-methylbenzyl o-toluate, is simultaneously carried out using a distillation column having 7 or more theoretical plates.

7. A process according to claim 1, wherein said distillation for removing said low boiling point components such as unreacted o-xylene and benzoic acid, and said high boiling point components, of which the major component is o-methylbenzyl o-toluate, is simultaneously carried out using a distillation column having 7 to 15 theoretical plates, to which the raw material is fed at a lower part to allocate at least one theoretical late for the striping section, under a pressure of 30 to 40 Torr., at a temperature of 150° to 230° C., and at a reflux ratio of 0.1 to 1, and drawing out said crude o-toluic acid at an upper point higher than the middle portion and lower than 1/5 of the column length from the top of the column.

8. A process according to claim 1, wherein said distillation after the treatment with ammonia is carried out using a distillation column having 10 or more theoretical plates.

9. A process according to claim 1, wherein said distillation after the treatment with ammonia is carried out using a distillation column having 10 to 30 theoretical plates, to which said crude o-toluic acid treated with ammonia is fed at a point below the middle of the column and where at least 2 theoretical plates are allocated for the stripping section, under a pressure of 100 to 300 Torr., at a temperature below 250° C., and at a reflux ratio of 3 to 20.

10. A process according to claim 5, wherein said distillation after the treatment with ammonia is carried out using a distillation column having 10 to 30 theoretical plates, to which said crude o-toluic acid treated with ammonia is fed at a point below the middle of the column and where at least 2 theoretical plates are allocated for the stripping section, under a pressure of 100 to 300 Torr., at a temperature below 250° C., and at a reflux ratio of 3 to 20.

11. A process according to claim 7, wherein said distillation after the treatment with ammonia is carried out using a distillation column having 10 to 30 theoretical plates, to which said crude o-toluic acid treated with ammonia is fed at a point below the middle of the column and where at least 2 theoretical plates are allocated for the stripping section, under a pressure of 100 to 300 Torr., at a temperature below 250° C., and at a reflux ratio of 3 to 20.

12. A process according to claim 1, wherein said treatment with ammonia is carried out using ammonia gas.

13. A process according to claim 10, wherein said treatment with ammonia is carried out using ammonia gas.

14. A process according to claim 11, wherein said treatment with ammonia is carried out using ammonia gas.

15. A process according to claim 1, wherein a fraction obtained by subjecting an oxidation product of o-xylene to distillation to remove therefrom low boiling point components such as unreacted o-xylene and benzoic acid contains not less than 3% by weight of o-methylbenzyl o-toluate.

* * * * *